(12) United States Patent
Hardy et al.

(10) Patent No.: US 11,173,111 B1
(45) Date of Patent: Nov. 16, 2021

(54) COMPOSITION AND METHOD FOR PREVENTION AND TREATMENT OF ANORECTAL DISORDERS

(71) Applicant: Rythera Therapeutics, Inc., Miami Lakes, FL (US)

(72) Inventors: Reginald L. Hardy, Ft. Lauderdale, FL (US); Mitchell Brigell, Belmont, MA (US)

(73) Assignee: Rythera Therapeutics, Inc., Miami Lakes, FL (US)

( * ) Notice: Subject to any disclaimer, the term of this patent is extended or adjusted under 35 U.S.C. 154(b) by 0 days.

(21) Appl. No.: 17/028,555

(22) Filed: Sep. 22, 2020

(51) Int. Cl.
*A61K 9/00* (2006.01)
*A61K 31/137* (2006.01)

(52) U.S. Cl.
CPC .......... *A61K 9/0031* (2013.01); *A61K 9/0053* (2013.01); *A61K 31/137* (2013.01)

(58) Field of Classification Search
CPC ... A61K 9/0031; A61K 9/0053; A61K 31/137
See application file for complete search history.

(56) References Cited

U.S. PATENT DOCUMENTS

| | | | | |
|---|---|---|---|---|
| 7,250,445 | B1 | 7/2007 | Ehrenpreis | |
| 7,776,844 | B2 | 8/2010 | Yu et al. | |
| 2008/0318931 | A1* | 12/2008 | Arkin | A61K 31/15 514/217 |
| 2016/0015818 | A1* | 1/2016 | Taha | A61K 9/0053 514/217 |
| 2017/0246267 | A1* | 8/2017 | Wang | A61K 31/27 |
| 2018/0140616 | A1* | 5/2018 | Jow | A61K 31/38 |

OTHER PUBLICATIONS

Vanneste et al. Chronic radiation proctitis: tricks to prevent and treat. Int J Colorectal Dis (2015) 30:1293-1303. (Year: 2015).*
McKinstry-Wu et al. Discovery of a Novel General Anesthetic Chemotype Using Highthroughput Screening. Anesthesiology. Feb. 2015 ; 122(2): 325-333. (Year: 2015).*
Grodsky, M.B., MD and Shafik M. Sidani, MD, Radiation Proctopathy, Clin Colon Rectal Surg (2015), 28:103-111.
Ghorbanzadeh-Moghaddam, A. et al., Vitamin D Deficiency is Associated With the Severity of Radiation-Induced Proctitis, Int'l J. Radiation Oncology Biol. Phys., vol. 92, No. 3, pp. 613-618 (2015).
Barton, M. and Dan Harris, Tricyclic antidepressant overdose: an unusual method of administration, BMJ Case Reports, 2010; doi:10.1136/bcr.04.2010.2914.
Kornhuber, J., et al., Identification of Novel Functional Inhibitors of Acid Sphingomyelinase, PLoS ONE Aug. 2011, vol. 6, Issue 8, e23852.
Corre, I., et al., Membrane Signaling Induced by High Doses of Ionizing Radiation in the Endothelial Compartment. Relevance in Radiation Toxicity. Int. J. Mol. Sci. (2013), 14, 22678-22696.
Guo, Y.R., et al., The Neuroprotective Effect of Amitriptyline on Radiation-Induced Impairment of Hippocampal Neurogenesis, Dose Response an International Journal, Oct.-Dec. 2019:1-8.
Adams, F., MD, Amitriptyline Suppositories, The New England Journal of Medicine (Apr. 22, 1982) p. 996.
Beckmann, N., et al., inhibition of Acid Sphingomyelinase by tricyclic antidepressants and analogons, Frontiers in Physiology (2014) vol. 5, Art. 331, www.frontiersin.org, doi: 10.3389/fphys.2014.00331.
Leonetti, D, et al., Secretion f acid sphingomyelinase and ceramide by endothelial cells contributes to radiation-induced intestinal toxicity, (online) cancerres.aacrjournals.org, Apr. 14, 2020, DOI: 10.1158/0008-5472.CAN-19-1527.
Shariati L, et al.. Protective effects of doxepin cream on radiation dermatitis in breast cancer: A single arm double-blind randomized clinical trial. Br J Clin Pharmacol 2020;86:1875-1881 https://doi.org/10.1111/bcp.14238.
BMJ Publishing Group (UK), Barton, M. and Dan Harris, Tricyclic antidepressant overdose: an unusual method of administration, all pages, Apr. 2010, BMJ Case Reports. DOI:10.1136/bcr.04.2010.2914.
PLoS ONE (Switzerland), H. Riezman (Ed.), Kornhuber, J., et al., Identification of Novel Functional Inhibitors of Acid Sphingomyelinase, Aug. 2011, vol. 6, Issue 8, e23852.
Open Access Publication (Germany), Beckmann, N., et al., Inhibition of Acid Sphingomyelinase by tricyclic antidepressants and analogous, pp. 1-14, Sep. 2014, Frontiers in Physiology, vol. 5, Art. 331. www.frontiersin.org, doi: 10.3389/fphys. 2014.00331.
American Association for Cancer Reesearch (US), Leonetti, D, et al., Secretion f acid sphingomyelinase and ceramide by endothelial cells contributes to radiation-induced intestinal toxicity, Apr. 14, 2020 (online publication) cancerres.aacrjournals.org. DOI: 10.1158/0008-5472.CAN-19-1527.

* cited by examiner

*Primary Examiner* — Robert A Wax
*Assistant Examiner* — Olga V. Tcherkasskaya
(74) *Attorney, Agent, or Firm* — Ted Whitlock Registered Patent Attorney, PA (57) ABSTRACT

A composition comprising at least one TCA useful in a method for treating an anorectal disorder, a rectal device and method of treating the anorectal disorder by anorectally administering an effective amount of the TCA, e.g. amitriptyline.

8 Claims, 2 Drawing Sheets

COMPOSITION AND METHOD FOR PREVENTION AND TREATMENT OF ANORECTAL DISORDERS

FIELD OF THE INVENTION

The invention is directed to methods, compositions and dosage forms or delivery devices for treating anorectal disorders. More specifically, the invention relates to methods and compositions for treating anorectal disorders such as radiation proctopathy or proctitis, using a tricyclic antidepressant (TCA), e.g., amitriptyline, a selective serotonin reuptake inhibitor (SSRI), e.g. sertraline, or a combination of a TCA and an SSRI, combination of one or more TCA, or combination of one or more SSRI, in a controlled release oral dosage form, suppository, or contained within a delivery device for rectal administration.

BACKGROUND OF THE INVENTION

A variety of disorders may affect the anorectal region, and may involve one or more of inflammatory, ischemic, infectious, traumatic, or neoplastic pathologies. Symptoms of anorectal disease include anal or rectal pain, urgency to move the bowels, fecal incontinence, diarrhea, rectal bleeding, and difficulty with evacuation of the rectum.

Radiation therapy administered for pelvic cancers such as cancers of the prostate, cervix, uterus, or ovary, can cause damage to the rectum resulting in a condition known as radiation proctopathy or proctitis. It is believed that the condition of radiation proctopathy or proctitis may result from the accumulation of ceramide following destruction of cells by the radiation. Inflammation of the rectum and anus are acute symptoms of radiation proctopathy or proctitis, but apoptosis and necrosis of the cells can result in radiation proctopathy or proctitis even years after radiation treatment is completed.

Attempts to prevent or treat radiation proctopathy or proctitis have been largely unsuccessful. Many topical treatments used for anorectal or lower bowel conditions appear to be ineffective. For example, use of the anti-inflammatory agent 5-aminosalicylic acid (5-ASA), previously used to treat Inflammatory Bowel Disease (IBD), was unsuccessful in treating radiation proctopathy or proctitis, with and without a steroid such as hydrocortisone. Sucralfate had also been recommended for radiation proctopathy but has proven ineffective.

Topical therapies, such as nitroglycerin and calcium channel blockers, were also found ineffective for treating radiation proctopathy. Short chain fatty acid enemas have also been used to treat radiation proctopathy but are not readily available and are difficult to administer.

Recently, antioxidants, such as Vitamin A, Vitamin C, and Vitamin E formulated in a suppository have been described for treating radiation proctopathy or proctitis. Suppositories are solid dosage forms comprising medications for placement in the anus or vagina for the treatment of certain systemic conditions but can be used for localized treatment of anorectal and gynecologic disorders. For example, one common use of rectal suppositories is for the treatment of constipation.

Rectal suppositories are also used as an alternative form of drug delivery in patients that cannot receive medications by mouth, whereby the medication is absorbed by the mucus membrane and distributed systemically. Examples of these types of rectal suppositories include treatments for nausea and pain.

It has been proposed that damage to healthy tissue from radiation therapy may involve an endothelial response associated with signaling from the plasma membrane, via the acid sphingomyelinase/ceramide pathway (Corre, I., et al., Intl. J. Mol. Sci. (2013) 14, 22678-22696.) Protecting against endothelial damage, for example, by inhibiting acid sphingomyelinase (ASMase) activity, is suggested as a means for limiting radiation toxicity in normal tissues. Although inhibitors of ASMase are known, none have been developed for local administration, nor demonstrated to be effective for prevention or treatment of radiation proctitis.

Amitriptyline has been formulated in a suppository dosage form. However, amitriptyline suppositories were only prepared for systemic delivery and to treat depression—the known indication for amitriptyline. Another indication for amitriptyline suppositories for systemic delivery is insomnia, exploiting the sleep-inducing side effect observed for amitriptyline. Amitriptyline suppositories have not previously been known to be administered to patients undergoing, or that have undergone, pelvic radiation therapy or for treating radiation proctopathy or proctitis or any other in situ treatment within the lower intestinal tract.

Tricyclic antidepressants, in general, have not previously been known to be used for treating anorectal disorders such as radiation proctopathy or proctitis. Nor have dosage forms comprising a tricyclic antidepressant such as amitriptyline been formulated for anal or rectal administration or in situ (or non-systemic) treatment of radiation proctopathy or proctitis. More specifically, amitriptyline has not previously been formulated in a dosage form, such as a suppository or other anorectal delivery device for localized treatment of radiation proctopathy or proctitis.

Nor has a tricyclic antidepressant, such as amitriptyline, been formulated as a controlled release formulation to bypass release within a low pH environment (acidic pH of less than 7), such as in the stomach, such that the drug release occurs primarily in the intestine, preferably the lower intestine for in situ delivery of the drug to treat radiation proctopathy or proctitis.

Selective serotonin reuptake inhibitors (SSRI's) are not known to be available in suppository form; nor are SSRI's known to be previously used for treatment of radiation proctopathy or proctitis.

There are numerous anorectal diseases that may benefit from localized administration of TCAs, such as amitriptyline or SSRIs, such as sertraline. These conditions include (but are not limited to), inflammatory bowel disease (IBD) including ulcerative proctitis and Crohn's disease, anal fissures, internal hemorrhoids, radiation proctopathy, anal and rectal neoplasms, anal warts, anal dysplasia, solitary rectal ulcer syndrome, pruritic ani and anorectal ischemia. These conditions represent a variety of significant clinical problems for which limited treatment options are currently available.

Thus, there is a need to develop methods and compositions and dosage forms or delivery devices that may be used to treat anorectal disorders such as radiation proctitis or proctopathy.

BRIEF SUMMARY OF THE INVENTION

The subject invention comprises a method for treating, ameliorating, or preventing an anorectal disorder or condition such as radiation proctopathy or proctitis using at least one tricyclic antidepressant (TCA) such as amitriptyline, or at least one selective serotonin reuptake inhibitor (SSRI)

such as sertraline. More specifically, the method of the invention comprises the step of:

anorectally administering to a patient in need thereof, such as a patient undergoing radiation treatment of the pelvic area or a patient suffering from radiation proctopathy or proctitis, a dosage form comprising a pharmaceutically effective amount of one or more active ingredients, wherein at least one active ingredient is a tricyclic antidepressant (TCA) or a selective serotonin reuptake inhibitor (SSRI) or any combination thereof.

Alternatively, a method according to the subject invention can comprise the step of:

orally administering to a patient in need thereof, such as a patient suffering from radiation proctopathy or proctitis, a controlled release dosage form comprising a pharmaceutically effective amount of one or more active ingredients, wherein at least one active ingredient is a tricyclic antidepressant (TCA) or a selective serotonin reuptake inhibitor (SSRI) or any combination thereof, wherein the controlled release dosage form provides in situ delivery of the one or more active ingredients to the lower intestine, preferably, the anorectal tissue of the patient.

One method for treating anorectal disorders according to the present invention involves in situ administration of a TCA, such as amitriptyline. The method includes a step of providing a composition comprising between about 0.1-1000 milligrams (mg) of a TCA, such as amitriptyline, and delivering the drug directly to the anorectal area, either as a topical composition, such as a cream or ointment, or formulated in a suppository or rectal plug dosage form.

One method for treating anorectal disorders according to the present invention involves in situ administration of an SSRI, such as sertraline. The method includes a step of providing a composition comprising between about 0.1-1000 milligrams (mg) of an SSRI, such as sertraline, and delivering the drug directly to the anorectal area, either as a topical composition, such as a cream or ointment, or formulated in a suppository or rectal plug dosage form.

One method for treating anorectal disorders according to the present invention involves in situ administration of a combination of a TCA, such as amitriptyline and an SSRI, such as sertraline. The method includes a step of providing a composition comprising between about 0.1-1000 milligrams (mg) of a TCA, such as amitriptyline, between about 0.1-1000 milligrams (mg) of an SSRI, such as sertraline, and delivering the drugs directly to the anorectal area, either as a topical composition, such as a cream or ointment, or formulated in a suppository or rectal plug dosage form.

In one preferred embodiment, the method comprises providing a solid suppository or rectal plug dosage form comprising the TCA and placing the dosage form within the rectal cavity for a period of time required for delivery of the active ingredient to the site. A preferred compound for use in accordance with the invention is amitriptyline, but other compounds within the class of TCAs may be substituted for amitriptyline or can be used in combination with amitriptyline or another TCA.

The invention further includes a composition comprising a TCA provided in a dosage form for rectal delivery of the TCA and treatment, amelioration, or prevention of radiation proctopathy or proctitis. Alternatively, the invention can include a composition comprising an SSRI provided in a dosage form for rectal delivery of the SSRI and treatment, amelioration, or prevention of radiation proctopathy or proctitis. The compositions can include one or more active ingredient selected from a TCA, an SSRI, and a composition of two different TCA's, two different SSRI's, or a TCA and an SSRI. For example, the invention can be provided as a suppository dosage form for use in treating anorectal disorders. Although not bound or restricted to any theory, it is contemplated that administration of amitriptyline or sertraline in a suppository form would be efficacious for radiation proctopathy and other chronic conditions of the rectum, because the suppository allows for delivery of an effective amount or concentration of drug directly to the affected area of the rectum and anus.

The suppository dosage form can comprise a soluble base and a TCA, e.g., amitriptyline, an SSRI, such as sertraline, or a combination of one or more TCA or SSRI, and can further include other pharmaceutically acceptable excipients as conventionally employed in suppository dosage forms.

Alternatively, the TCA or SSRI or combination can be included within rectal plug comprising pores that allow delivery of the drug from the plug to the site following administration. The TCA or SSRI or combination can be formulated as a suppository which can be housed within the porous rectal plug.

Yet another alternative dosage form comprises an anal or rectal plug comprising a soft, compressible, porous material (e.g., a foam rubber or polymeric sponge-like material) wherein the TCA, SSRI or combination active ingredient or ingredients are infiltrated or infused within, or coated on, the porous compressible plug material.

Preferably, the TCA or SSRI or combination is provided in a controlled-release formulation which allows delivery of the drug over a period of time as compared to an immediate-release formulation which provides delivery of all the drug from the dosage form as soon as it is administered.

According to a preferred embodiment, the TCA contained within the suppository or rectal plug dosage form is amitriptyline at a dosage of between 1-1000 mg milligrams (mg); more preferably a dose of about 5 mg-150 mg, and most preferably a dose of about 10 mg-100 mg, a 50 mg dose being one preferred dose. In another preferred embodiment, the SSRI contained within the suppository or rectal plug dosage form is sertraline at a dosage of between 1-1000 mg milligrams (mg); more preferably a dose of about 5 mg-150 mg, and most preferably a dose of about 10 mg-100 mg, a 50 mg dose being one preferred dose. The dose contained within the suppository or rectal plug can vary, being lower in dosage forms that more rapidly deliver drug to the site, or higher in dosage forms that slowly release drug to the site. In addition, where two or more actives are provided in the suppository, the concentration of each active may be lower than when used as a single active ingredient, and thereby advantageously lowering the dose of each and the consequent risk of side effects.

According to a further aspect of the invention, the suppository or rectal plug can include an additional active ingredient, which is not a TCA or an SSRI. For example, the suppository or rectal plug dosage form can include a TCA or SSRI and an anti-inflammatory agent or a TCA or SSRI and an anesthetic agent.

A tricyclic antidepressant useful in the method of the invention includes administering an effective amount of one or more of: amineptine, amitriptyline, amoxapine, butriptyline, clomipramine, desipramine, dibenzepin, dosulepin, doxepin, imipramine, iprindole, lofepramine, maprotiline, norclomipramine, northiaden, nortriptyline, opipramol, protriptyline, tianeptine, or trimipramine. A preferred tricyclic antidepressant is amitriptyline.

Examples of selective serotonin reuptake inhibitors useful in accordance with the subject invention include, but are not limited to, citalopram, escitalopram, fluoxetine, fluvoxamine, paroxetine, and sertraline. A preferred selective serotonin reuptake inhibitor for purposes of the subject invention is sertraline.

Preferably, the method is carried out using a TCA or SSRI formulated as a composition provided in dosage form which can deliver an effective dose in situ to the rectal cavity of the patient. For example, the TCA or SSRI active ingredient can be formulated as a liquid and administered as an enema, or can be formulated with a thickening agent or viscosity-enhancing agent to provide a lotion, cream, ointment or gel for topical or intra-anal delivery of the tricyclic antidepressant to an anorectal area and rectal cavity of the patient.

In the method employing a solid dosage form, such as a suppository or a rectal plug delivery device for delivery of the TCA or SSRI or combination to the anorectal cavity and in situ administration of the drug, the dosage form can be provided with or incorporated into the rectal plug delivery device as a controlled release formulation, having one or more excipient that can retard the release of active drug incorporated into the dosage form or which is coated onto the outer surface of the dosage form or a particle, granule or bead within the dosage form comprising the active ingredient. A controlled release dosage form can also be provided for oral administration wherein the oral dosage form is formulated as a delayed release dosage form which bypasses the acidic environment in the stomach and releases active ingredient in intestinal tract where the pH is above 7.0. Such controlled release dosage forms can be formulated using an enteric coating on a tablet, provided within delayed release capsule or caplet, formulated in a slow release matrix composition, or a combination of the above.

Where the dosage form is a rectal plug delivery device, the device can be an insoluble plug forming a housing which has an internal chamber for containing therewithin a composition comprising the TCA, SSRI, or combination. For example, the chamber of the rectal plug can be filled with a viscous composition comprising a TCA or can contain a suppository dosage form comprising the TCA active ingredient.

An alternative embodiment of a rectal plug delivery device useful for carrying out the method of the invention comprises a porous compressible foam material infused or coated with a composition comprising the TCA, e.g., amitriptyline, SSRI, e.g., sertraline, or combinations thereof. The devices described for the method of the invention can contain an effective dose of the TCA or SSRI or combination between about 0.1 mg to about 1000 mg or greater.

The method of the invention can further include the administration to a patient in need thereof of at least one TCA or SSRI or combination and an additional active ingredient. Preferably, the additional active is formulated together with the at least one TCA or SSRI or combination in a fixed-dose combination drug product. The additional active ingredient can be a different TCA than the first TCA active ingredient, a different SSRI from a first SSRI active ingredient, or can be an active ingredient in a different class of drug than a TCA or SSRI.

One preferred embodiment of composition having two active ingredients and the second active is not a TCA or SSRI is a composition comprising a first active ingredient which is a TCA or an SRI, and a second active ingredient which is an anti-inflammatory, anesthetic agent, or an antioxidant. The anti-inflammatory can be a steroid or a non-steroidal anti-inflammatory (NSAID). The anesthetic agent can be a local anesthetic commonly used for topical administration, such as lidocaine. The antioxidant can be, for example, Vitamin A, Vitamin C, Vitamin D, and Vitamin E.

The subject invention includes a composition for treating radiation proctopathy or proctitis comprising an effective amount of a TCA or SSRI or combination of at least two TCA's, at least two SSRIs, or at least one TCA and at least one SSRI, formulated as a controlled release formulation for in situ delivery of the antidepressant to the rectal cavity. In one preferred embodiment, the composition can be formulated as a controlled release suppository containing at least one TCA as the active ingredient. The composition can include an SSRI, or can include a TCA or SSRI and an additional active ingredient as described herein.

The TCA, SSRI, or combination contained in a suppository or rectal delivery device can be administered prior to, during, or following pelvic radiation therapy. A preferred administration includes inserting the suppository or rectal delivery device into the rectal cavity and allowing the suppository or rectal delivery device to remain within the rectal cavity until delivery of the entire dose is completed. A preferred suppository in accordance with the invention can slowly dissolve and remain for a period of up to about 24 hours, i.e., daily use. A rectal plug delivery device can be retained within the rectal cavity for a period of up to about 48 hours but is preferred to include a drug formulation which delivers the dose of the active ingredient or ingredients within about 24 hours. This provides for daily use following a bowel movement. Alternatively, the rectal plug can be temporarily removed for bowel movements and re-inserted.

It would be understood that the method, dosage form and delivery device of the invention can be useful for preventing, treating or ameliorating other anorectal conditions or disorders such as inflammatory bowel disease (which includes ulcerative colitis or proctitis and Crohn's disease), anal fissure, internal hemorrhoids, anal and rectal neoplasms, anal warts, anal dysplasia, solitary rectal ulcer syndrome, pruritic ani and anorectal ischemia, or the like.

DETAILED DESCRIPTION OF THE INVENTION

A variety of chronic, painful, and debilitating disorders may affect the anorectal region. Examples of these disorders include IBD (ulcerative proctitis and Crohn's disease). Ulcerative proctitis is a chronic idiopathic disorder characterized by inflammation (edema, ulceration, and bleeding) of the lining of the rectum. In anorectal Crohn's disease, chronic inflammation extends throughout the wall of the rectum and anus, resulting in deep ulcerations, fissuring and abscess formation as well as the findings seen in ulcerative colitis.

Anal fissure, when chronic, is a longstanding ulcer of the anoderm or skin surrounding the anus. Internal hemorrhoids are enlarged veins inside the anal canal that may become inflamed, causing bleeding and anal pressure. Radiation proctopathy, a consequence of prior radiation for pelvic cancers causes defecation disorders due to damage and stiffness of the rectal wall and bleeding from new blood vessels that form as a response to decreased local blood flow. Neoplasms are abnormal growths of the anorectal region and may cause pain, ulcerations, and rectal bleeding. Anorectal cancer generally occurs in patients developing anal warts from a virus called Human Papilloma Virus (HPV). Long-standing anorectal infection with HPV causes dysplasia which may degenerate into anal cancer. Solitary rectal ulcer syndrome occurs from decreased blood flow to the rectum due to anal spasm and prolapsing of the rectal wall through the anal canal. Large ulcerations and rectal bleeding commonly are present in patients with solitary rectal ulcer syndrome. Pruritis ani or anal itching occurs in part from abnormalities of the anal sphincter. Anorectal ischemia results from diminished blood supply to the anus and rectum related to a variety of conditions affecting the vascular system.

The present invention provides an innovative method for treating these conditions in mammals, including humans and can employ the use of a novel composition or dosage form, or a novel delivery device to administer the treatment.

One embodiment of the invention relates to a method for treating radiation proctopathy or proctitis by administering an effective amount or dose of an active ingredient, such as a tricyclic antidepressant (TCA), a selective serotonin reuptake inhibitor (SSRI), or a combination of two different TCA's, two different SSRI's or at least one TCA and at least one SSRI.

Examples of TCAs useful in accordance with the subject invention are amineptine, amitriptyline, amoxapine, butriptyline, clomipramine, desipramine, dibenzepin, dosulepin, doxepin, imipramine, iprindole, lofepramine, maprotiline, norclomipramine, northiaden, nortriptyline, opipramol, protriptyline, tianeptine, and trimipramine. The invention includes the use of at least one TCA and can include the use of at least two different TCAs or can include the use of three or more different TCAs. Another embodiment of the invention includes the use of at least one TCA and a second active ingredient which is not a TCA.

A preferred TCA for use in accordance with the subject invention is amitriptyline. Amitriptyline, marketed in the United States under the brand name ELAVIL® (AstraZeneca PLC, Cambridge England) is primarily used to treat a number of mental illnesses, including major depressive disorder, anxiety disorders, and less commonly attention deficit hyperactivity disorder (ADHD) and bipolar disorder. Other uses include prevention of migraines, treatment of neuropathic pain such as fibromyalgia and postherpetic neuralgia, and less commonly insomnia.

Examples of SSRI's useful in accordance with the subject invention are citalopram, escitalopram, fluoxetine, fluvoxamine, paroxetine, and sertraline. The invention includes the use of at least one SSRI and can include the use of at least two different SSRI's or can include the use of three or more different SSRI's. Another embodiment of the invention includes the use of at least one SSRI and an additional active ingredient which is not an SSRI.

For purposes of the subject invention, reference to "active," "active agent," "active ingredient," "active pharmaceutical ingredient," or derivations of these terms, as well as "drug," or "drug product," means a drug or class of drug which is a direct or indirect inhibitor of acid sphingomyelinase (ASMase). An indirect inhibitor includes a functional inhibitor of ASMase, or FIASMA. An ASMase inhibitor can affect the formation, accumulation, or release of ceramide and, unless expressly specified or clarified by context of the description, specifically refers to:

1. A tricyclic antidepressant (TCA), such as amitriptyline;
2. A selective serotonin reuptake inhibitor (SSRI), such as sertraline;
3. A fixed dose combination of two or more TCA's, wherein each is a different and within the class of TCA;
4. A fixed dose combination of two or more SSRI's, wherein each is a different and within the class of SSRI;
5. A fixed dose combination of at least one TCA and at least one SSRI;
6. A fixed dose combination of at least one TCA and an additional drug which is not a TCA or SSRI;
7. A fixed dose combination of at least one SSRI and an additional drug which is not a TCA or SSRI; or
8. A fixed dose combination of at least one SSRI and at least one TCA and an additional drug which is not a TCA or SSRI;

or a composition, included a drug product or dosage form comprising the drug.

Amitriptyline has not previously been known to be useful for treatment of radiation proctopathy or proctitis. Sertraline has not previously been known to be useful for treatment of radiation proctopathy or proctitis.

Rectal administration of an active ingredient of the invention in a suppository form or by employing a rectal plug delivery device, can provide at least the following advantages: 1) larger doses can be delivered directly to the diseased area, resulting in better therapy for the conditions; 2) the amount of the delivered substance can undergo much less or no absorption into the systemic circulation; and 3) provides in situ delivery of the active ingredient to the anorectal tissue affected by radiation treatment administered to the pelvic area. Although not bound or restricted to any theory, it is contemplated that administration of amitriptyline in a suppository form would have even greater efficacy for radiation proctopathy and other chronic conditions of the rectum, since the suppository allows for delivery of effective amounts of a TCA, such as amitriptyline, directly to the affected area of the rectum and anus.

In a preferred embodiment, the active pharmaceutical ingredient is incorporated into a suppository or rectal plug delivery device for administration and placement into the rectum and rectal cavity for the treatment of anorectal diseases, conditions, or disorders. This treatment is preferably administered in a suppository form or rectal plug delivery device for patients suffering from chronic anorectal disorders. These treatments may be administered once daily, or more or less frequently as determined by the patient's physician or healthcare provider.

Suppository dosage forms are well known in the art and are used conventionally in medical treatments. "Suppository," as used herein, means a solid substance that is administered into the rectum that contains medication and which dissolves or melts following administration for anorectal delivery. Suppositories may be constructed from fatty (or oleaginous) bases and/or water soluble (or miscible) bases using conventional formulation methods. A preferred embodiment in accordance with the subject invention is to incorporate a carbomer, gelling agent, such as a cellulosic hydrogel, wax, polymeric material, or other controlled release agent into the composition forming the suppository, or other topical lotion, cream, gel, or ointment comprising the active agent of the invention.

The suppository dosage form can comprise a soluble base and an active pharmaceutical ingredient, e.g., amitriptyline, sertraline or a combination of amitriptyline and sertraline, and can further include other pharmaceutically acceptable excipients as conventionally employed in suppository dosage forms. The active ingredient can be formulated as a suppository which can be housed within a cavity formed in the porous rectal plug. Fatty bases include *Theobroma* oil (also known as cocoa butter) with or without spermacetic or beeswax to raise the suppository melting point. Additionally, fatty bases for the amitriptyline suppositories may include synthetic triglycerides and hydrogenated vegetable oils. These may include palm, palm kernel or coconut oils. Name brands utilized for production of amitriptyline suppositories may include Fattibase, Wecobee FS, M, R or S, Dehydag, Hydrokote, Suppocire and Witepsol. Water soluble bases may include glycerated gelatin, with or without preservatives, and polyethylene glycol polymers.

Suppositories may be constructed by hand rolling, compression molding or fusion molding methods.

In another embodiment of the invention, the active ingredient, such as one or more TCA, e.g., amitriptyline, one or more SSRI, e.g., sertraline, or combinations thereof, can be formulated for oral administration. Preferably, the oral dosage form is provided as a controlled release dosage form. Delayed release formulations can be created by coating a solid dosage form with a polymeric film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon.

Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGIT® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied. Polymer blends can be used to achieve the desired delay in drug release.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The term "anorectal disease" refers to and includes the group of abnormal conditions or disorders occurring in humans or animals that produce characteristic gastrointestinal symptoms and are associated with appropriate findings on physical examination or endoscopy.

The term "proctitis" used in the invention refers to inflammation of the lining of the rectum. "Proctopathy" is used to denote a disorder of the rectum causing alteration of rectal function, but not limited to disorders resulting from inflammation.

"Radiation proctopathy or proctitis" refers to a disorder of the rectum causing alteration of rectal function, including inflammation of the lining of the rectum, resulting from radiation therapy of the pelvic area. Radiation therapy of the pelvic area is a known and accepted treatment procedure for cancer of urogenital tissue, for example, treating prostate cancer in men, or treating cervical cancer in women. The term is used herein as it is clinically understood by physicians that treat such disorders.

The present invention provides a method for treating anorectal disorders by in situ administration of an active pharmaceutical ingredient of the invention, such as a TCA, e.g., amitriptyline, an SSRI, e.g., sertraline, or combinations thereof. The method includes a step of providing a composition comprising between about 0.001-10 grams of the active ingredient, and delivering the drug directly to the anorectal area, either as a topical composition, such as a cream or ointment, or formulated in a suppository or rectal plug dosage form. According to a preferred embodiment, a TCA contained within the suppository or rectal plug dosage form is amitriptyline at a dosage of between 1-1000 milligrams (mg); more preferably a dose of about 5 mg-150 mg, and most preferably a dose of about 10-100 mg, where one preferred dosage is a suppository or other dosage form comprising about 50 mg. In another preferred embodiment, an SSRI contained within the suppository or rectal plug dosage form is sertraline at a dosage of between 1-1000 milligrams (mg); more preferably a dose of about 5 mg-150 mg, and most preferably a dose of about 10-100 mg, where one preferred dosage is a suppository or other dosage form comprising about 50 mg. The dose contained within the suppository or rectal plug can vary, being lower in dosage forms that more rapidly deliver drug to the site, or higher in dosage forms that slowly release drug to the site. In addition, where two or more active pharmaceutical ingredient are provided in a fixed dose combination suppository product, the dose of each of the active ingredients may be reduced within the dosage form and thereby advantageously lower the risk or incidence of side effects.

Preferably, the method comprises providing a solid suppository or rectal plug dosage form comprising a composition having a TCA or SSRI as an active ingredient and placing the dosage form within the rectal cavity for a period of time required for delivery of the active ingredient to the site. The composition provided within the rectal plug delivery device can be a suppository.

Alternatively, the drug can be delivered using a rectal delivery device such as a rectal plug containing an effective dose of active ingredient, such as a TCA, SSRI or combination thereof. In one embodiment of a rectal plug device according to the invention, the plug device comprises an insoluble porous housing forming a chamber for containing the active ingredient. The active ingredient can be provided as a soluble suppository disposed within a chamber portion formed within the porous rectal plug housing. The suppository is exposed to bodily fluids when administered to cause dissolution and in situ delivery of the active ingredient from the suppository. In a preferred embodiment, the suppository is formulated as a controlled release formulation. Alternatively, the active ingredient can be formulated as a viscous, controlled release gel, ointment, or cream for filling the chamber within the rectal plug housing.

Other types of rectal plugs are known and can be adapted for use in accordance with the subject invention. For example, rectal plugs formed of a porous sponge-like polymeric material, such as polyurethane foam, are known for use in fecal incontinence. Such rectal plugs are marketed under the name PERISTEEN™ Anal Plug (Coloplast Corp., North Minneapolis, Minn., USA). The polyurethane foam can be infused with a solution comprising an effective amount of a TCA or the effective amount of TCA can be adsorbed onto the material for delivery when inserted into the rectal cavity. These commercially available rectal plugs generally are provided in a compressed configuration for ease of insertion and are wrapped with a water-soluble film which dissolves following insertion and can expand to an extended configuration. Such compression and expansion are not required for in situ delivery of drug in accordance with the subject invention.

Figure 1:
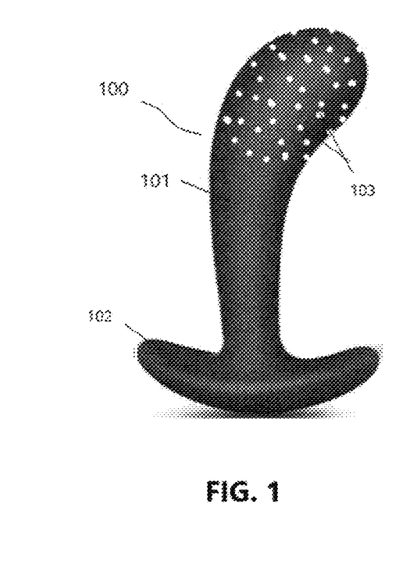
FIG. 1 shows perspective view of a rectal plug device having a projecting member and a flange member, where the projecting member comprises a housing depicted as having pores and bounding a chamber for containing a soluble dosage form comprising at least one active ingredient, such as a TCA, an SSRI, or a combination thereof.
Figure 2:
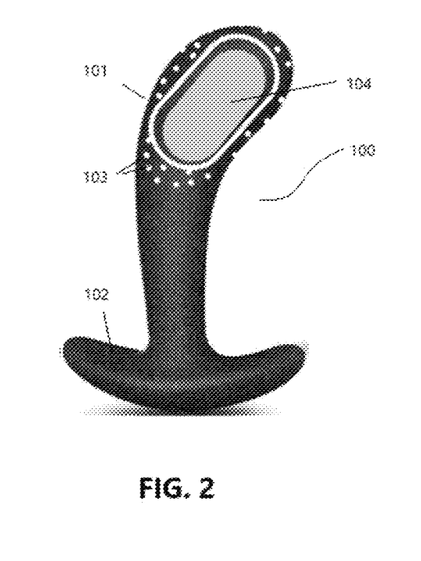
FIG. 2 shows a rectal plug of FIG. 1 in cross-section, illustrating the dosage form disposed within the chamber.

FIGS. 1 and 2 illustrate one example of a rectal plug delivery device for use in accordance with the invention. FIG. 1 shows a rectal plug delivery device 100 comprising an elongate member 101 which forms the proximal end of the device which is inserted into and resides within the rectal cavity during delivery of the active ingredient. The rectal plug delivery device can comprise a distal flange 102 to prevent the entirety of the rectal plug delivery device from being taken up into the rectal cavity, thereby holding the rectal plug device in place during administration of the active ingredient. The active ingredient, such as a TCA or SSRI, can be provided as a pharmaceutical composition which is housed within a cavity (not shown) formed within the elongate member. The proximal end of the elongate member 101 comprises pores 103 for allowing bodily fluids to enter the cavity formed within the elongate member, and to allowing egress of the active ingredient from the composition contained within the elongate member. The rectal plug delivery device can have an extension piece connected to the distal flange, such as a strap or string, to facilitate removal of the rectal plug delivery device, functioning similarly to removal of a tampon.

FIG. 2 shows a sectioned view of the rectal plug delivery device 100 of FIG. 1, illustrating the cavity formed within the proximal end of the elongate member 101, which can contain the composition 104 comprising active pharmaceutical ingredient. As illustrated, the composition can be formed as a suppository, which dissolves or melts when administered within the rectal cavity. Alternatively, the composition can be an amorphous, or unformed, composition comprising a gel, cream, or ointment. Preferably, the composition is provided as a controlled-release composition, preferably an extended-release composition, which releases the active ingredient from the composition over time.

In another embodiment, the dosage form comprises an anal plug comprising a soft, compressible, porous material (e.g., a foam rubber or polymeric sponge-like material) wherein the active ingredient is infiltrated or infused within, or coated on, the porous compressible plug material. This embodiment is illustrated in FIGS. 3 and 4.

Figure 3:
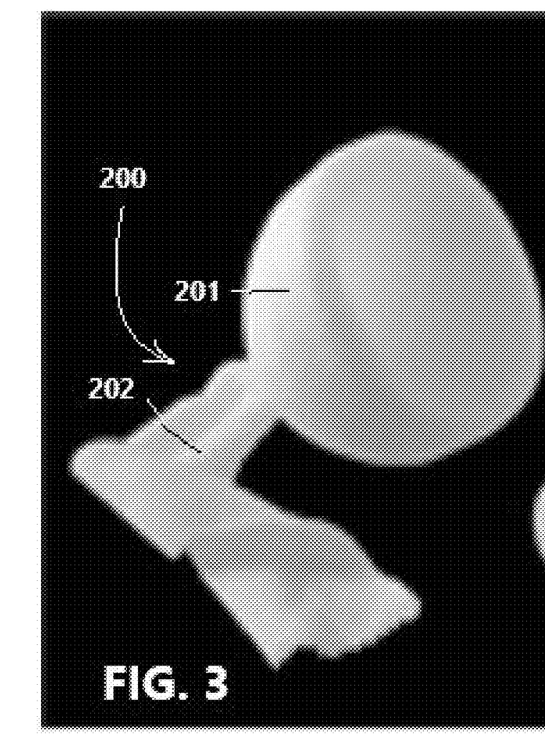
FIG. 3 shows a perspective view of an alternative embodiment of a rectal plug of the invention comprising a porous compressible foam material infused or coated with a composition comprising a TCA or SSRI or combination and is depicted in its expanded configuration after administration.

FIG. 3 shows a rectal plug delivery device 200 comprising a soft, compressible, porous material in an expanded configuration. The rectal plug delivery device 200 comprises at its proximal end a drug delivery component 201 which expands when inserted into the rectal cavity, and conforms to the shape of the rectal cavity. Connected to the drug delivery component is an extension piece 202, such as a strap or string, to facilitate removal of the rectal plug delivery device, functioning similarly to removal of a tampon.

The composition comprising active ingredient according to the invention can be infused or infiltrated into the porous material forming the delivery component 201, as a liquid or gel, cream, or ointment. The composition comprising the active ingredient can be provided as a controlled-release composition, preferably an extended-release composition, which releases the active ingredient over time.

Figure 4:
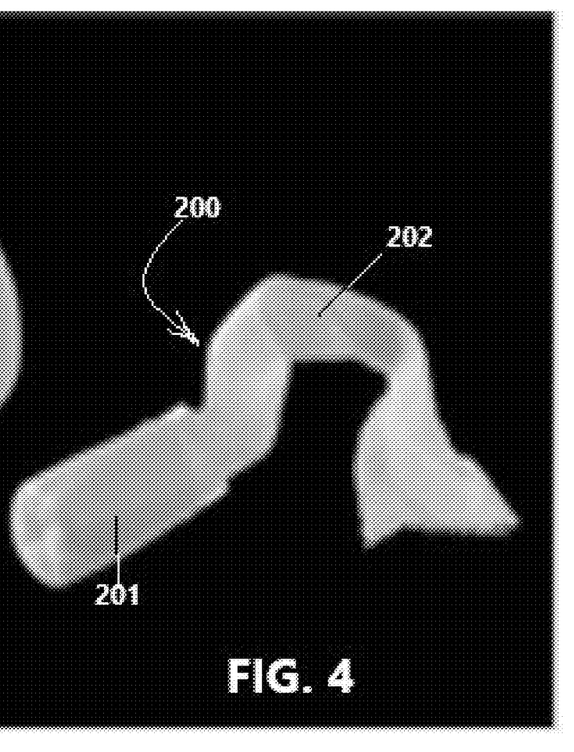
FIG. 4 shows a perspective view of the porous compressible foam rectal plug of FIG. 3, in a compressed configuration prior to administration.

FIG. 4 shows the rectal plug delivery device 200 of FIG. 3, wherein drug delivery component 201 is provided in compressed form, for ease of insertion into the rectal cavity. The compressed drug delivery component 201 can include a water-soluble wrapper surrounding the drug delivery component 201. Following insertion of the rectal plug delivery device embodiment 200 into the rectal cavity, bodily fluids dissolve the wrapper and allow the drug delivery component 201 to expand to its expanded configuration as shown in FIG. 3. FIG. 4 further shows extension piece 202, which can be a strap or string, to facilitate removal of the rectal plug delivery device.

Preferably, the active ingredient is provided in a controlled-release formulation which allows delivery of the drug over a period of time as compared to an immediate-release formulation which provides delivery of all the drug from the dosage form as soon as it is administered. Controlled release formulations known in the art include the use of coatings, such as enteric-coated tablets, beads, or pellets, ion exchange resins, waxes, alginates, gelling agents, such as cellulosic hydrogels (e.g., hydroxypropyl methyl cellulose, or HPMC) or polymeric acrylamides (e.g., CARBOPOL®) formulated with an active agent, and a suitable vehicle which melts or dissolves in rectal fluids. Such formulations and compositions, as well as methods of manufacturing suppositories or other controlled-release compositions are well known in the art.

In a method according to the invention, treating, ameliorating, or preventing an anorectal disorder or condition such radiation proctopathy or proctitis employs a composition comprising at least one active pharmaceutical ingredient according to the invention, such as amitriptyline (as an example of a TCA) or sertraline (as an example of an SSRI). The composition employed in the method of the invention can be provided in a suppository dosage form.

In addition, the subject invention comprises a method for treating, ameliorating or preventing an anorectal disorder or condition such radiation proctopathy or proctitis using a comprising at least one TCA such as amitriptyline, or at least one SSRI such as sertraline. More specifically, these suppository compositions or rectal delivery devices described herein are useful in a method for preventing, treating or ameliorating radiation proctopathy or proctitis.

The method of the invention comprises the step of:
anorectally administering an effective dose of one or more active ingredients, namely a drug in the class selected from a TCA, an SSRI, or a combination thereof, to the rectal cavity of a patient in need thereof, such as a patient suffering from radiation proctopathy or proctitis.

A preferred method of the invention comprises anorectally administering an effective dose of an active ingredient, such as the TCA, amitriptyline. Alternatively, a preferred method of the invention comprises anorectally administering an effective dose of an active ingredient, such as the SSRI sertraline. Compositions comprising a fixed dose combination two or more different TCA's, two or more different SSRI's, at least one TCA and at least one SSRI, or the above with an additional active ingredient which is not a TCA or SSRI can also be used. In one preferred example, the method is carried out using amitriptyline formulated as a composition and provided in dosage form which is capable of delivering an effective dose in situ to the rectal cavity of the patient. For example, amitriptyline can be formulated as a liquid and administered as an enema, or can be formulated with a thickening agent or viscosity-enhancing agent to provide a lotion, cream, ointment or gel for topical delivery of amitriptyline to an anorectal area and rectal cavity of the patient.

Alternatively, the method can employ a solid dosage form, such as a suppository or a rectal plug delivery device for delivery of the active pharmaceutical ingredient to the anorectal cavity and in situ administration of the drug. Preferably, the dosage form provided with or incorporated into the rectal plug delivery device is a controlled release formulation, having excipients that retard the release of active drug incorporated into the dosage form or coated onto the outer surface of the dosage form.

Where the dosage form is a rectal plug delivery device, the device can be an insoluble plug forming a housing which has an internal chamber for containing therewithin a composition comprising the active pharmaceutical ingredient in accordance with the invention. For example, the chamber of the rectal plug can be filled with a viscous composition comprising amitriptyline or can contain a suppository dosage form comprising amitriptyline as the active ingredient.

An alternative embodiment of a rectal plug delivery device useful for carrying out the method of the invention comprises a porous compressible foam material infused or coated with a composition comprising the active pharmaceutical ingredient in accordance with the subject invention. The devices described for the method of the invention can contain an effective dose of the TCA or SSRI between about 0.1 mg to about 1000 mg or greater.

The method of the invention can further include the administration to a patient in need thereof of at least one active ingredient and an additional active ingredient which is not a TCA or SSRI. Preferably, the additional active is formulated together with the at least one TCA, at least one SSRI, or a combination TCA and SSRI in a fixed-dose combination drug product.

One preferred embodiment of composition having a first and second active comprises a TCA or an SSRI and an anti-inflammatory, anesthetic agent, or an antioxidant. The anti-inflammatory can be a steroid or a non-steroidal anti-inflammatory (NSAID). The anesthetic agent can be a local anesthetic commonly used for topical administration, such as lidocaine. The antioxidant can be, for example, Vitamin A, Vitamin C, Vitamin D, and Vitamin E.

The subject invention includes a composition for treating radiation proctopathy or proctitis comprising an effective amount of a TCA or SSRI formulated as a controlled release formulation for in situ delivery of the active ingredient to the rectal cavity. In one preferred embodiment, the composition can be formulated as a controlled release suppository containing at least one TCA or at least one SSRI, or at least one TCA and one SSRI, as the active ingredient or ingredients. The composition can include an additional drug which is not a TCA or SSRI as described herein.

The active pharmaceutical ingredient contained in a suppository or rectal delivery device can be administered prior to, during, or following pelvic radiation therapy. A preferred administration includes inserting the suppository or rectal delivery device into the rectal cavity and allowing the suppository or rectal delivery device to remain within the rectal cavity until delivery of the entire dose is completed. A preferred suppository in accordance with the invention can slowly dissolve and remain for a period of up to about 24 hours, i.e., daily use. A rectal plug delivery device can be retained within the rectal cavity for a period of up to about 48 hours but is preferred to include a drug formulation which delivers the dose of the active ingredient or ingredients within about 24 hours. This provides for daily use following a bowel movement. Alternatively, the rectal plug can be temporarily removed for bowel movements and re-inserted.

The suppository containing active pharmaceutical ingredient is placed to reside within the rectal cavity for the time period required for dissolution. Since the suppositories are fully dissolvable, release of active ingredient from the suppository will be achieved after residence of the suppository in the rectum. The released active ingredient will occur in high concentrations at the site of delivery, thus enhancing the effectiveness of this therapy for anorectal disorders.

According to an alternative embodiment, the suppository may consist of other drugs or supplements, such as antioxidants, including vitamin E and vitamin C and natural antioxidants such as fish oils, green tea, cranberry, etc. These may be used as distinct suppository preparations or as additional components of the suppositories of the invention.

These uses and in any of the embodiments of the invention, a suppository form of these agents is used as a clinical treatment for chronic diseases of the anus and rectum.

Any form of the active ingredients contemplated by the invention that is placed in a suppository form for the treatment of anorectal diseases is within the confines of the invention. Additionally, the incorporation of active pharmaceutical ingredients described herein in combination with other active or inactive ingredients into suppositories to treat anorectal diseases is embodied within this invention. Additionally, the incorporation of any ASMase inhibitor within the suppositories as a means of treating anorectal disorders is embodied in the invention. Finally, other agents, such as anti-inflammatories, anesthetics, herbals, or other vitamins may be included in the suppositories to enhance the efficacy of the active ingredient or ingredients. Substances utilized to produce the suppositories include any fatty (or oleaginous) bases and/or water soluble (or miscible) bases.

In particularly preferred embodiments, the medication contained in the suppository is amitriptyline. In the preferred embodiment, the suppository is composed of fatty (or oleaginous) bases and/or water soluble (or miscible) bases. However, other bases may be employed in the invention to allow for the passage of the medication into the rectum. More generally, any form of suppository base may be used to construct the devise. In addition, a variety of TCAs may be incorporated into the suppository to allow direct application of these substances to the rectum and anus. Other aforementioned substances may also be included in the suppositories to enhance their efficacy in treating anorectal disorders. The contents of the suppository may also consist of a variety of TCAs, either alone or in combination with amitriptyline, depending on the goal of treatment.

Variable doses of amitriptyline may be utilized, depending on the condition being treated. For example, the rectal dose of amitriptyline used for the treatment of radiation proctopathy is 25-100 mg a day. Both lower and higher doses than these would initially be employed in the construction of the devise. The optimal dosage to treat these conditions will be determined based on clinical studies.

However, following appropriate clinical evaluation of this treatment, either larger or smaller doses of amitriptyline may ultimately be used for treating radiation proctopathy as well as other anorectal disorders. Dosing for amitriptyline and other TCAs in suppositories are anticipated to be lower than oral doses for the treatment of anorectal diseases because these agents will be directly applied to the affected areas. However, because the delivery by suppository or rectal device does not need to be ingested and the dosage forms can be larger in size, higher doses than typically employed in oral dosage forms may also be utilized if so determined safe and effective based on further clinical experience or studies.

The foregoing description of the invention is illustrative only and is not intended to limit the scope of the invention to the precise terms set forth. Further, although the invention has been described in detail with reference to certain illustrative embodiments, variations and modifications exist within the scope and spirit of the invention as described and defined in the following claims.

The invention claimed is:

1. A method for treating or ameliorating radiation proctopathy, said method comprising:
   providing a sertraline composition consisting of 1-100 mg of sertraline and pharmaceutically acceptable excipients per 1 ml of said composition;
   topically applying the sertraline composition to a rectal tissue of a patient in need thereof, prior to, during, or following pelvic radiation therapy, whereby 1-100 mg of sertraline is administered per day to the rectal tissue.

2. The method of claim 1, wherein the sertraline composition is administered anorectally.

3. The method of claim 1, wherein the sertraline composition is in a form of a lotion, a cream, an ointment, or a gel for topical delivery of the sertraline composition to an anorectal area and rectal cavity of the patient.

4. The method of claim 3, wherein the sertraline composition is provided in a dosage form selected from a suppository or a rectal plug delivery device for delivery of the sertraline composition to the anorectal cavity.

5. The method of claim 4, wherein the rectal plug delivery device comprises a porous housing containing the sertraline composition, wherein the porous housing of the rectal plug is insoluble when delivered to the anorectal area for administration of the sertraline composition.

6. The method of claim 4, wherein the dosage form is a suppository.

7. The method of claim 1, wherein an effective dose of the sertraline is 50 mg.

8. A method for treating or ameliorating radiation proctopathy, said method comprising:
   providing a composition consisting of (i) 1-100 mg per ml of a first active ingredient which is sertraline; (ii) a second active ingredient selected from the group consisting of a local anesthetic and an antioxidant; and (iii) pharmaceutically acceptable excipients; and wherein the local anesthetic is lidocaine, and wherein the antioxidant is selected from the group consisting of vitamin A, vitamin C, vitamin D, and vitamin E; and
   administering the composition to a rectal tissue of a patient in need thereof prior to, during, or following pelvic radiation therapy, whereby 1-100 mg of sertraline is administered per day to the rectal tissue.

* * * * *